(12) United States Patent
Biedermann et al.

(10) Patent No.: US 8,257,399 B2
(45) Date of Patent: Sep. 4, 2012

(54) ANCHORING DEVICE FOR ANCHORING A ROD IN BONES OR VERTEBRAE

(75) Inventors: Lutz Biedermann, Villingen (DE); Wilfried Matthis, Weisweil (DE); Gerhard Pohl, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 281 days.

(21) Appl. No.: 12/333,873

(22) Filed: Dec. 12, 2008

(65) Prior Publication Data

US 2009/0163956 A1    Jun. 25, 2009

Related U.S. Application Data

(60) Provisional application No. 61/013,618, filed on Dec. 13, 2007.

(30) Foreign Application Priority Data

Dec. 13, 2007  (EP) .................................... 07024221

(51) Int. Cl.
*A61B 17/70* (2006.01)

(52) U.S. Cl. ........ 606/265; 606/264; 606/300; 606/305; 606/306; 606/279

(58) Field of Classification Search .................. 606/246, 606/264–279, 300–321
See application file for complete search history.

(56) References Cited

U.S. PATENT DOCUMENTS

| 5,658,284 | A | 8/1997 | Sebastián et al. |
| 5,873,878 | A | 2/1999 | Harms et al. |
| 6,077,262 | A * | 6/2000 | Schlapfer et al. ............ 606/305 |
| 7,857,834 | B2 | 12/2010 | Boschert |
| 2003/0100896 | A1 | 5/2003 | Biedermann et al. |
| 2003/0100904 | A1 | 5/2003 | Biedermann |
| 2004/0176766 | A1 | 9/2004 | Shluzas |
| 2005/0059972 | A1 | 3/2005 | Biscup |

(Continued)

FOREIGN PATENT DOCUMENTS

DE    41 10 002 C1    5/1992

(Continued)

OTHER PUBLICATIONS

European Search Report for European Application No. 07024221.9 filed Dec. 13, 2007 in the name of Biedermann Motech GmbH, European Search Report dated May 14, 2008 and mailed May 25, 2008 (6 pgs.).

*Primary Examiner* — Eduardo C Robert
*Assistant Examiner* — Christina Negrelli
(74) *Attorney, Agent, or Firm* — Christie, Parker & Hale, LLP

(57) ABSTRACT

An anchoring device for anchoring a rod in a bone or a vertebra and for use with at least two rods having a different diameter is provided. The anchoring device includes a shaft and a head for connection to one of said rods. The head is connected to said shaft and has a recess with a base and two substantially vertically extending legs defining a channel for receiving the rod in said channel. The anchoring device further includes a fixation element for clamping said rod in said channel. The fixation element and said base each have a contact surface contacting said rod, the contact surfaces being shaped so as to be able to clamp any of the different rods.

21 Claims, 8 Drawing Sheets

U.S. PATENT DOCUMENTS

2005/0261687 A1* 11/2005 Garamszegi et al. ........... 606/61

FOREIGN PATENT DOCUMENTS

| DE | 199 12 364 A1 | 10/2000 |
| EP | 1 316 294 A2 | 11/2002 |
| JP | 08-056957 | 3/1996 |
| JP | 9-506283 | 6/1997 |
| WO | WO 95/25473 | 9/1995 |

* cited by examiner

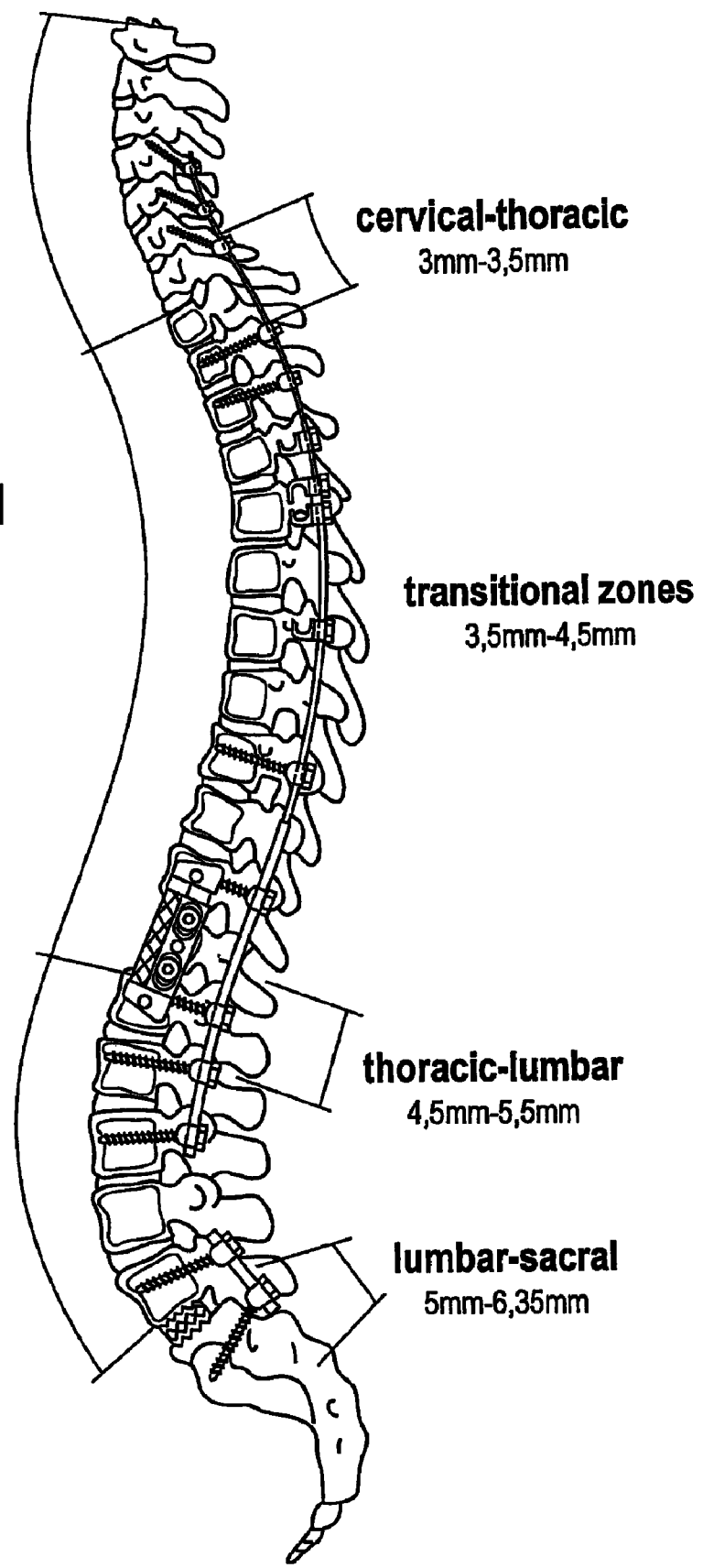

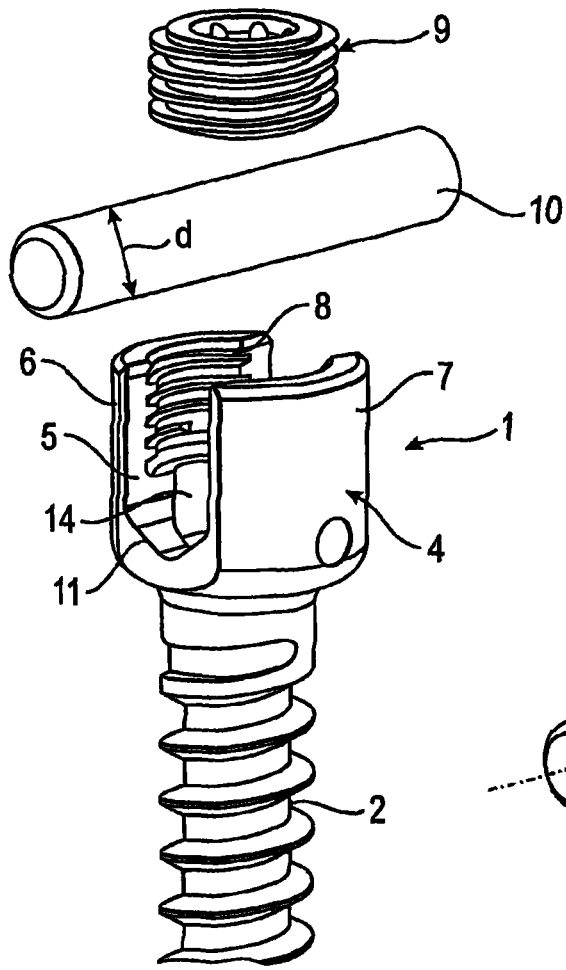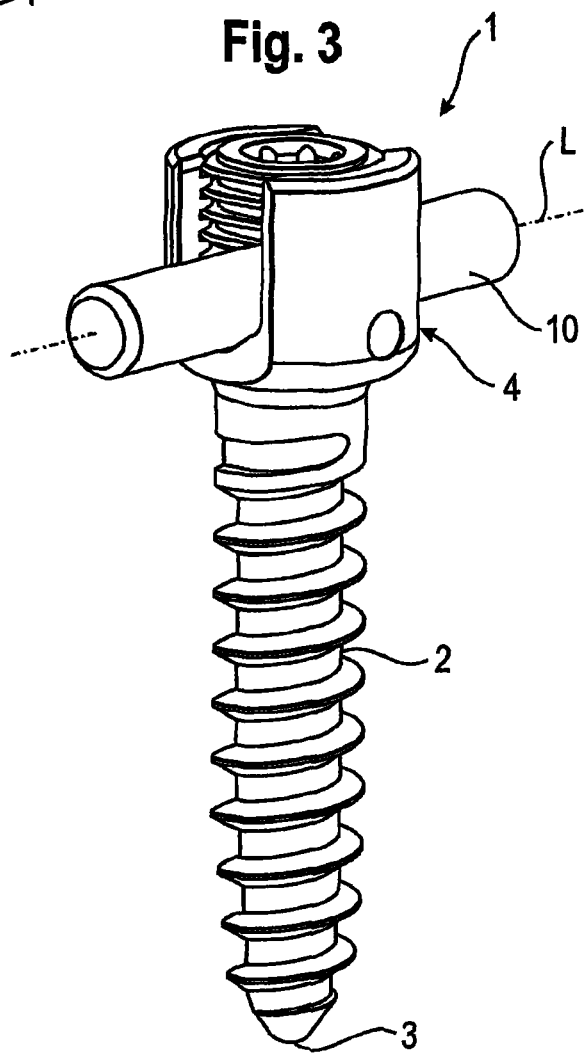

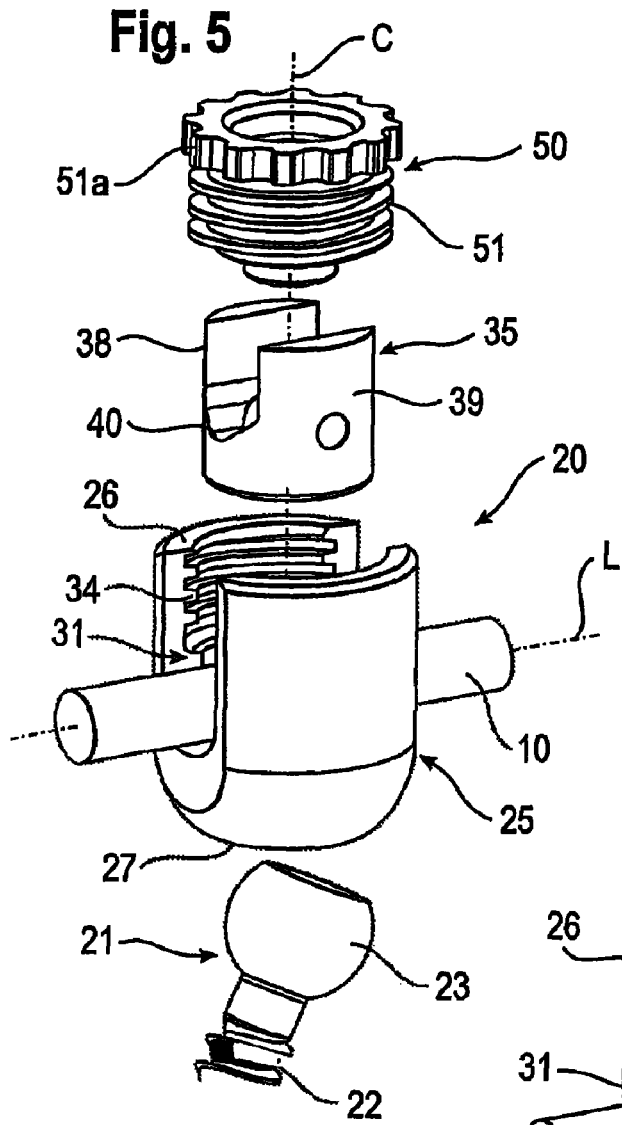
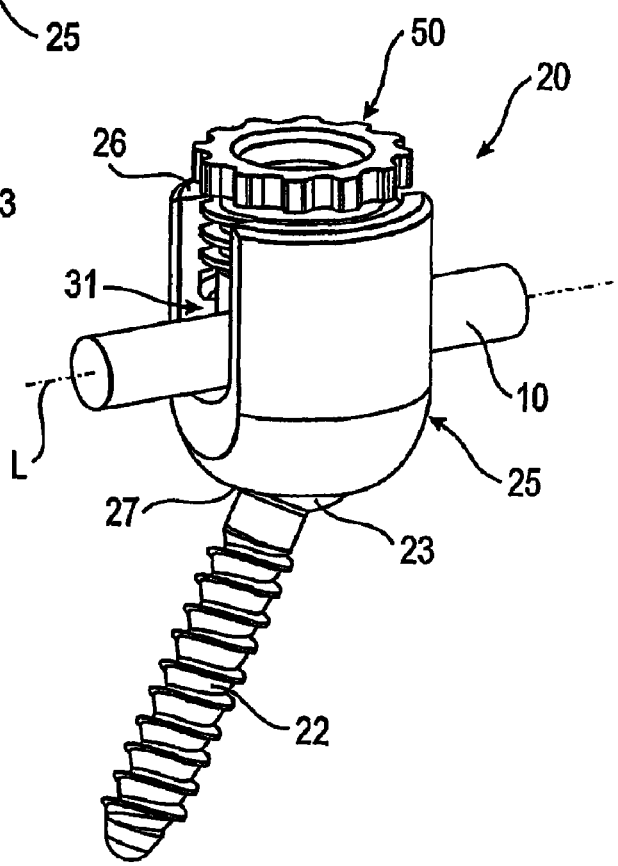

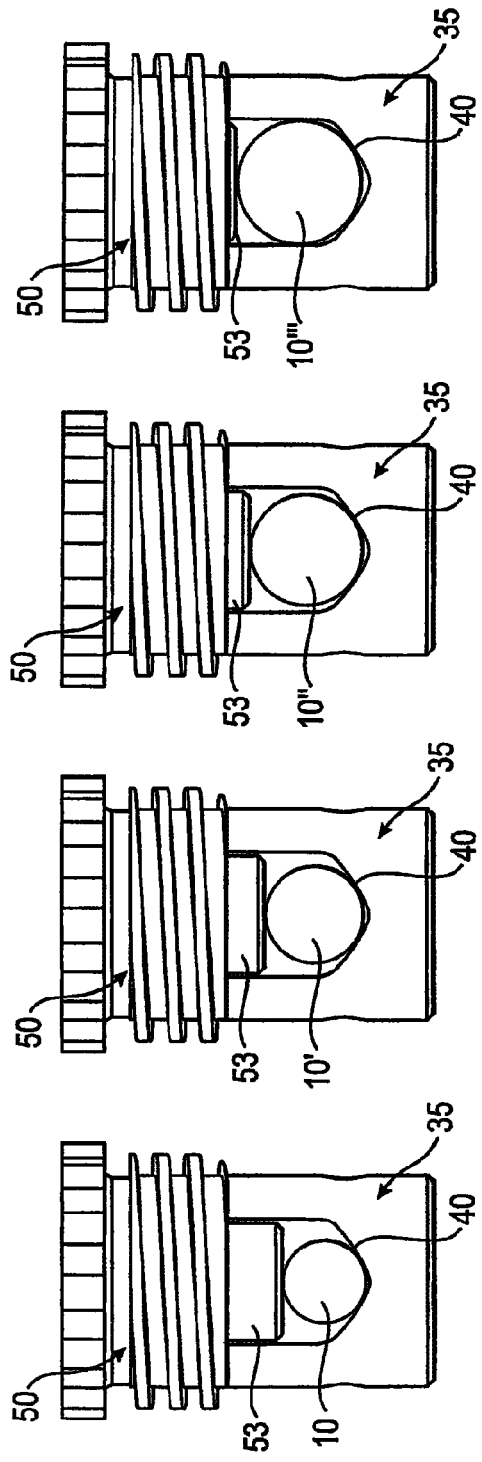
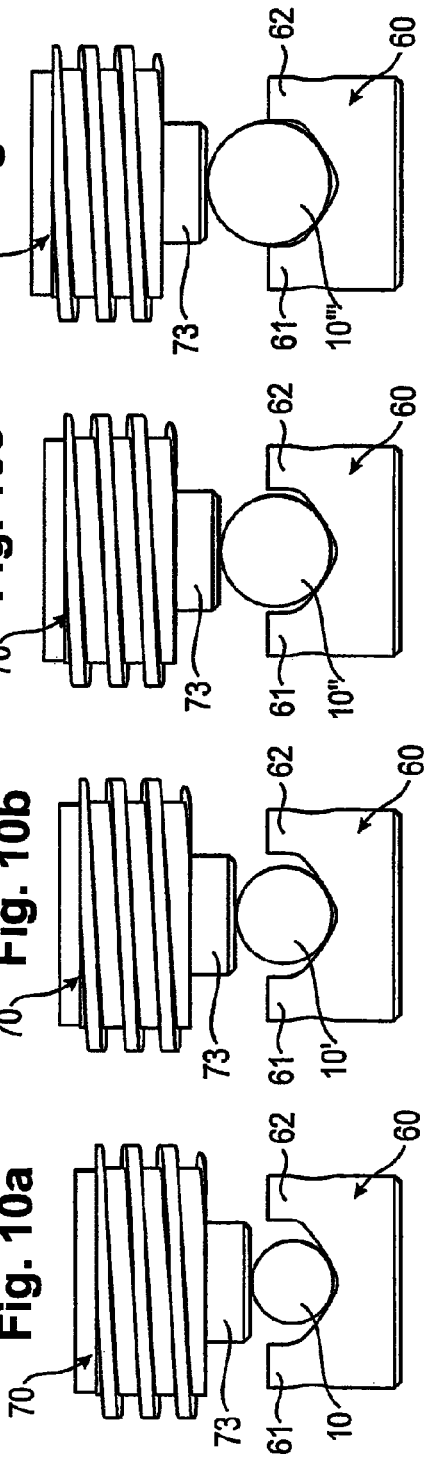

ANCHORING DEVICE FOR ANCHORING A ROD IN BONES OR VERTEBRAE

CROSS-REFERENCE TO RELATED APPLICATION(S)

The present application claims the benefit of U.S. Provisional Patent Application Ser. No. 61/013,618, filed Dec. 13, 2007, the contents of which are hereby incorporated by reference in their entirety, and claims priority from European Patent Application EP 07 024 221.9, filed Dec. 13, 2007, the contents of which are hereby incorporated by reference in their entirety.

BACKGROUND

The invention relates to an anchoring device for anchoring a rod in bones or vertebrae which can be used with at least two rods having a different diameter.

For stabilizing the spinal column, bone anchoring devices are known which comprise a shaft to be anchored in the bone and a head to be connected to a rod. Usually, a rod connects several bone anchoring devices. Depending on the medical indication and the region of the spine where the stabilization is required rods with different diameters are needed. The diameter of the rods ranges from 3 mm to more than 6 mm. Generally, the diameter of the rod which is used in the lower part of the spine is larger than the diameter of the rod which is used in the upper part of the spine. For example, as shown in FIG. 1 in the cervical-thoracic region of the spine rods with a diameter of 3 mm to 3.5 mm, in the transitional zones between the cervical-thoracic and the thoracic-lumbar region rods with a diameter of 3.5 mm to 4.5 mm, in the thoracic-lumbar region rods of usually 4.5 mm to 5.5 mm and the lumbar-sacral region rods with a diameter of 5 mm to 6.35 mm are necessary.

Typical bone anchoring devices have a recess for receiving a rod. The diameter of the recess may be slightly larger than the diameter of the rod in order to account for small variations in manufacturing tolerances. The tolerance may allow rod diameter variation of about 2%. However, the noted tolerance is not sufficient to allow the use of different diameter rods as discussed above for different spinal surgery applications.

For each diameter of the rod, specific bone anchoring devices, such as pedicle screws, are required. They differ from each other in particular by the size of the recess into which the rod is inserted. The provision of having different bone anchoring devices available for surgery increases the costs and renders spinal surgery more complicated for surgeon.

U.S. Pat. No. 5,873,878 discloses an anchoring member for attachment to a vertebra and for use with a first rod having a first diameter and a second rod having a second, smaller diameter. The anchoring member has an insert member which can be inserted into the head of the anchoring member so as to allow the insertion of a rod with a smaller diameter.

Based on the above, there is a need to provide an anchoring device which can be used with several rods having a different diameter.

SUMMARY OF THE INVENTION

An anchoring device according to the disclosure can provide a safe clamping of any of the rods having a different diameter. The clamping force does not depend on the diameter of the rod.

Furthermore, the bone anchoring device is constructed to minimize the number of parts. Hence it does not require additional parts to allow the fixation of different rods.

The anchoring device can be used in particular for the correction of scoliosis in children. When the child grows up, it may be necessary to adapt the scoliosis correction device. For example, it may be necessary to use other rods with a greater diameter as those originally inserted. With the bone anchoring device according to the invention it is possible to replace the originally used rods in a second surgery with the bone anchors remaining anchored in the vertebrae.

BRIEF DESCRIPTION OF THE DRAWINGS

Further features and advantages of the invention will become apparent and will be best understood by reference to the following detailed description of embodiments taken in conjunction with the accompanying drawings.

FIG. 1 shows a schematic view of the spinal column with spinal stabilization devices using rods of different diameter in different regions of the spine.

FIG. 2 shows a perspective exploded view of the anchoring device according to a first embodiment.

FIG. 3 shows a perspective view of the bone anchoring device of FIG. 2 in an assembled state.

FIG. 5 shows a perspective exploded view of the anchoring device according to a second embodiment.

FIG. 6 shows a perspective view of the anchoring device of FIG. 5 in an assembled state.

FIG. 9a to d shows schematically the clamping of the rod in the pressure element shown in FIGS. 8a to 8d), where different rods having different diameters are used.

FIG. 10a to 10d show schematically the clamping of rods having different diameters in a pressure element of a modified embodiment.

DETAILED DESCRIPTION OF THE INVENTION

Figure 4:
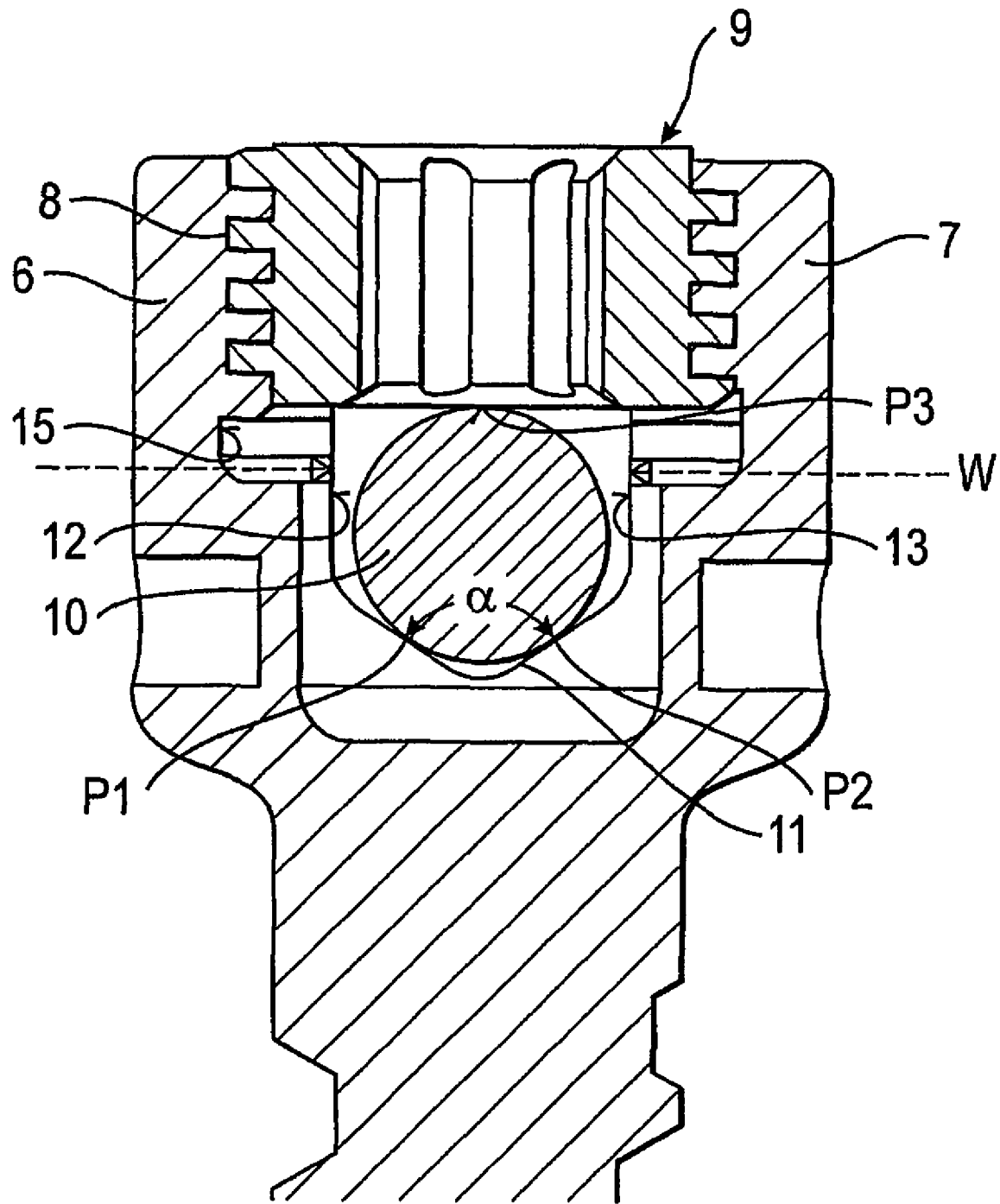
FIG. 4 shows a sectional view of the anchoring device of FIG. 3 in an assembled state, the section being taken perpendicular to the rod axis.

The anchoring device according to a first embodiment of the invention is described with reference to FIGS. 2 to 4. The anchoring device 1 includes a shaft 2 with a tip 3 at one end and a head 4 at the other end. The shaft has a bone thread in at least a portion thereof.

The head 4 has on its side opposite to the tip a recess 5 which forms two free legs 6, 7 are formed defining a channel for receiving a rod 10. An internal thread 8 is provided at the legs 6, 7 for receiving an inner screw 9 for fixation of the rod 10 in the channel. The rod has a circular or substantially circular cross section.

By the recess 5 two opposite and substantially vertical flat side walls 12, 13 are formed as best seen in FIG. 4. The distance of the side walls 12, 13 and hence, the width of recess 5 is slightly larger than the largest diameter of a rod to be accommodated in the recess, so that the rod can be inserted and guided therein in the direction of the rod axis L. The base 11 of the recess 5 has a substantially V-shaped cross section, as can be particularly seen in FIG. 4. The bottom of the base 11 is rounded. The angle α defined by the V-shape of the base 11 is such that the rod 10 with the diameter d contacts the base at two opposite line contacts P1, P2, extending in a direction parallel to the rod axis L.

In the center of channel, an axial bore 14 as shown in FIG. 2 is provided so that the V-shaped base 11 of the recess 5 is provided on either side of the legs 6, 7. Having an internal hole formed by the axial bore 14 allows to achieve a multi-point contact, which means left and right contact. This is especially important for pre-bent and contoured rods.

The internal thread 8 which is provided on the legs 6, 7 extends from the free end of the head 4 over a predetermined length. Adjacent to the internal thread 8 an undercut 15 is provided in the direction towards the base 11. In the embodiment shown in FIGS. 2 to 4, the inner screw 9 is a set screw which can be screwed between the legs. When the rod 10 is inserted and the inner screw 9 is screwed in, it presses onto the rod with its lower side facing the rod when it is tightened. Hence, the inner screw 9 contacts the rod 10 along a contact line P3.

The dimensions of the width W of the recess 5 and the V-shaped base 11 as well as the diameter d of the rod 10 and the length of the inner screw 9 are such that the rod 10 is clamped along the three contact lines P1, P2 and P3. The rod is in a stable position when it is clamped in this way, similar to a three-point fixation in the locking section. This achieves a secure multi-line contact along the rod. It should be understood that the contact lines are not infinitesimally thin lines but are lines which have a certain thickness according to the contact which is macroscopically generated. This provides a safe fixation independently of the diameter of the rod.

The diameter of the rod which can be used with the anchoring device may vary between a largest diameter and a smallest diameter which are defined geometrically in such a way that the rod has in any case two lines of contact with the base 11. The length of the inner screw 9 is such that when the inner screw is fully screwed in, it touches the rod at the contact P3. The arrangement of the V-shaped base 11 and the length of the inner screw 9 is such that rods that vary in diameter by about 14% or more can be used in the recess 5 and clamped along contact lines P1, P2 and P3 as described herein.

The anchoring device and the rod are made of a biocompatible material, for example of a metal such as titanium or a metal alloy, such as for example an alloy exhibiting superelastic properties. The rod is rigid in such a sense that it is held in place by frictional forces when the inner screw is tightened.

In use, first at least two anchoring devices are anchored with their shafts in the bone, for example in the pedicle of a vertebra. Then, a rod for spinal stabilization is selected which has a specific diameter suitable for the clinical application. The rod is inserted into the recesses and fixed by tightening the inner screws.

A second embodiment is described with reference to FIGS. 5 to 8. The anchoring device 20 is a polyaxial bone screw which includes a screw element 21 with a shaft 22 with a bone thread and a spherical head 23. The spherical head 23 has a recess 24 on its free end serving for engagement with a screw tool.

The anchoring device further includes a receiving part 25 which has a first end 26 and a second end 27 opposite to the first end and a central axis C. Coaxially with the central axis C, a bore 29 is provided which extends from the first end to a distance from the second end. At the second end, an opening 30 is provided the diameter of which is smaller than the diameter of the bore 29. The head 23 is pivotably held in the receiving part with the shaft extending through the opening 30.

The receiving part further has a substantially U-shaped recess 31 starting at the first end and extending in the direction of the second end. The U-shaped recess 31 defines two free legs 32, 33. An internal thread 34 is provided on the legs.

A pressure element 35 is provided which has a substantially cylindrical construction with an outer diameter which is only slightly smaller than the inner diameter of the bore 29 to allow the pressure element to be introduced into the bore and to be moved therein in an axial direction. On its lower side facing towards the head 23 of the screw element 21, the pressure element 35 comprises a spherical recess 36 the radius of which corresponds to the radius of the spherical head 23 of the screw element. On the opposite side the pressure element comprises a recess 37 which forms two legs 38, 39 with flat side walls 38', 39' and a base 40. The base 40 is substantially V-shaped similar to the base 11 of the first embodiment. It can be rounded at its deepest point and transition to the flat side walls. The angle α' which is defined by the side walls of the base 40 is sized in such a way that a rod with a largest diameter and one with a smallest diameter can be inserted so that they contact the base 40 at two contact lines P1, P2 parallel to the rod axis L, respectively. The depth of the recess 37 is such that for all rods having a diameter between the smallest and the largest diameter, the legs 38, 39 extend above the upper surface of the inserted rod. The pressure element further includes a coaxial bore 41 which serves for accessing the recess 24 of the head 23 with a screw tool.

Figure 7:
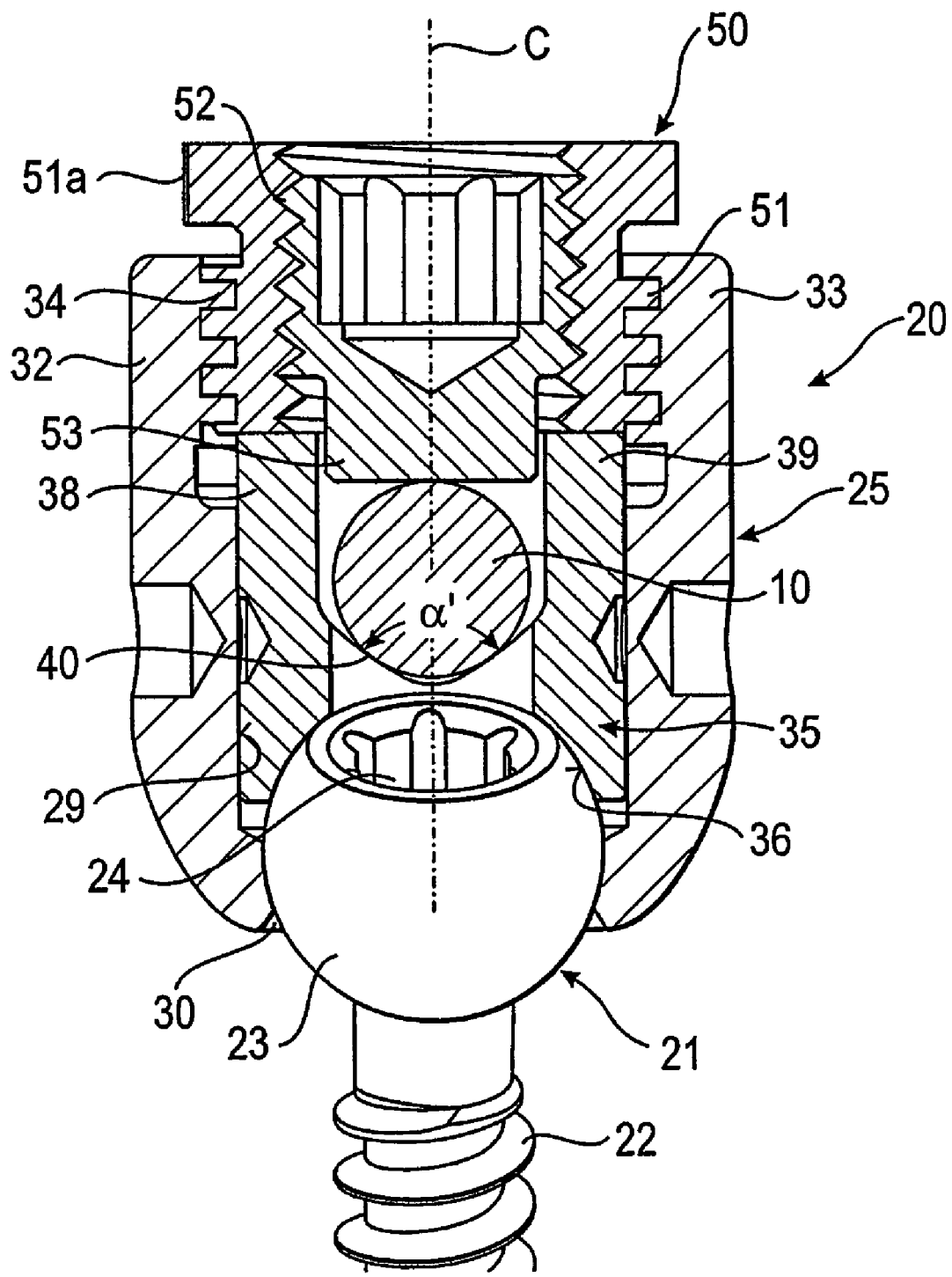
FIG. 7 shows a partial sectional view of the anchoring device of FIG. 6, the section being taken in a plane perpendicular to rod axis and through the center of the anchoring device.
Figure 8A:
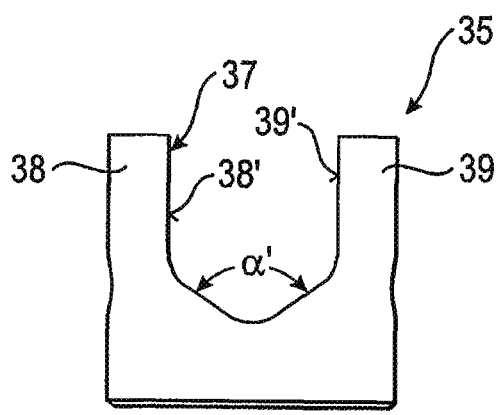
FIG. 8a shows a side view of the pressure element of the anchoring device of FIG. 7.
Figure 8B:
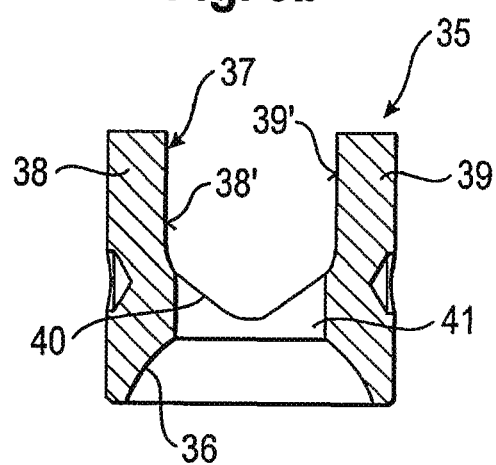
FIG. 8b shows a sectional view of the pressure element of the anchoring device of FIG. 7, the section being taken in a plane perpendicular to the rod axis.
Figure 8C:
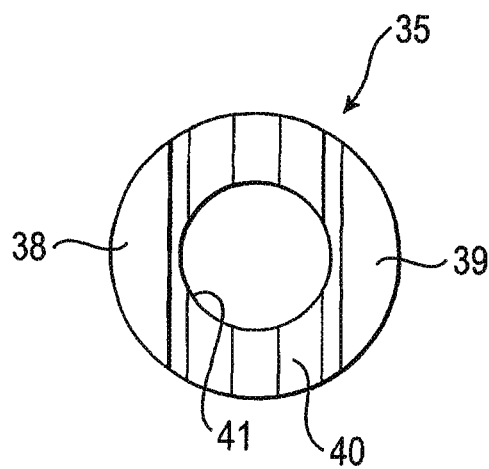
FIG. 8c shows a top view of the pressure element of the anchoring device of FIG. 7.
Figure 8D:
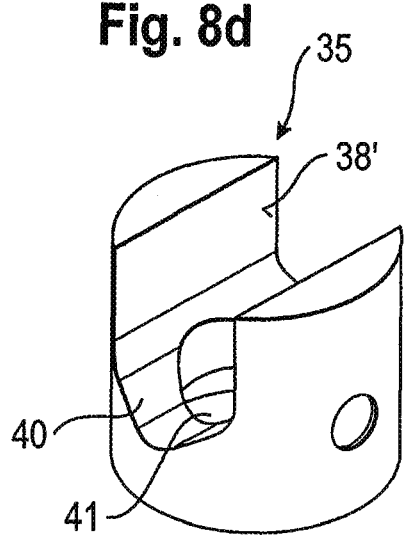
FIG. 8d shows a perspective view of the pressure element of the anchoring device of FIG. 7.

For fixation of the rod 10 and of the head 23 of the screw element 21, a fixation element 50 is provided. The fixation element 50 is a two part fixation element and includes a first outer screw 51 which cooperates with the internal thread 34 of the receiving part 25 and which has a coaxial threaded bore in which a second inner screw 52 is inserted. The first screw 51 comprises at its one end facing away from the receiving part an annular projection 51a with a structure for facilitating gripping of the fixation element. The first screw 51 presses with its lower side onto the legs 38, 39 of the pressure element when it is tightened, as shown in FIG. 7, without touching the inserted rod. Hence the first screw can fix the pivotal position of the head 23 by pressing the pressure element 35 onto the head 23.

The second screw 52 acts onto the rod 10. For being able to come into contact with rods of different diameters, the second screw comprises a projection 53 at its lower side which faces the rod, the projection being, for example, cylindrical and having a diameter smaller than the width of the recess 37 of the pressure element. Therefore, the projection 53 touches the rod but not the pressure element 35. The projection 53 is a structure used to balance the different rod diameters. By tightening the second, inner screw 52, the rod 10 can be fixed independently of the head 23.

In the assembled and fixed state as shown in FIGS. 6 and 7 the base 40 of the pressure element is projecting slightly above the base of recess 31 of the receiving part so that the rod 10 rests still in the base 40 of the pressure element.

Use of the device is similar to the first embodiment with the only difference being that the pivotal position of the screw element can be fixed by the first screw and the pressure element. The base of the pressure element then serves as the seat for a rod with a desired diameter between the largest and the smallest possible diameter.

FIGS. 9a to 9c show schematically the fixation of rods 10, 10', 10" and 10''' with increasing diameter. The rods in each case rest on the base on two points or, when seen three-dimensionally, on two contact lines. From above they are clamped by the inner screw of the fixation element which contacts the rod by the projection 53. Hence, each rod is in a stable clamping position similar to a three-point clamping. This allows use of rods of any diameter between the largest and the smallest possible diameter.

FIGS. 10a to 10c show schematically the fixation of rods 10, 10', 10" and 10''' with increasing diameter which differs from the second embodiment by the pressure element and the fixation element. The pressure element 60 has legs 61, 62 which do not extend above the upper surface of the inserted rod. The fixation element 70 is a single part fixation element in form of a set screw cooperation with the internal thread 34 of the receiving part 25 according to the second embodiment. The fixation element has a projection 75 acting onto the rod. With this embodiment, the head 23 and the rod 10 are fixed simultaneously.

Figure 11A:
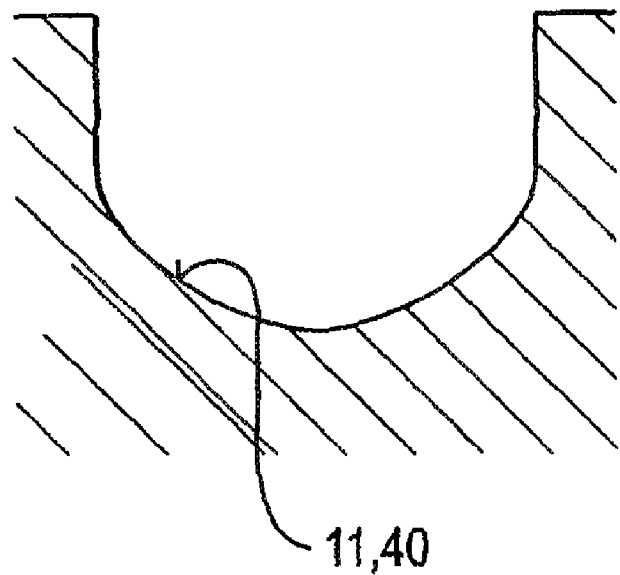
FIG. 11a to 11b show modified embodiments of the seat of the rod.
Figure 11B:
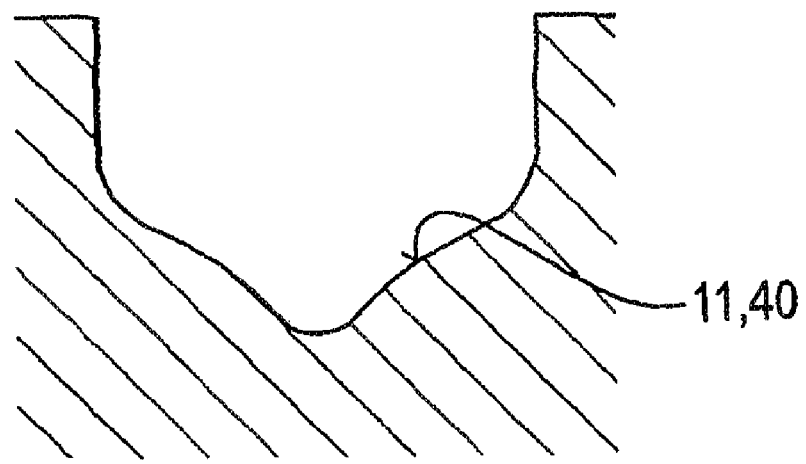

FIGS. 11a and 11b show a modification of the shape of the base 11 or 40, respectively. The side walls which form the V are not flat but curved. In FIG. 11a the base has concavely curved side walls, while in FIG. 11b the base has convexly curved side walls. Also in this modified embodiment, the rod rests in the base along two contact lines.

Modifications of the embodiments described are possible. For example, between the base in which the rod rests and the side walls of the recess in which the rod is inserted there can be areas like a step or an inclined surface.

The polyaxial screw is shown as a top loading screw i.e. the screw element is inserted from the first end or top of the receiving part, but it can also be designed as a bottom loading screw i.e. the screw element can be inserted into the receiving part designed therefor from the second end, i.e. the bottom.

It is also conceivable that the three line fixation is reversed, i.e. two lines are formed at the lower side of the fixation element and one contact point or line is formed at the base.

Combination of the features of the different embodiments are also possible.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. An anchoring assembly for anchoring a rod to a bone or a vertebra, the anchoring assembly comprising:
   a bone anchoring device comprising:
      a shaft; and
      a head connected to said shaft and having a recess with a base having a contact surface, the head further comprising two substantially vertically extending legs spaced apart by a first distance and defining a channel;
   a fixation element having a contact surface facing the contact surface of the base of the head, the fixation element secured to the legs and configured to move sufficiently into and out of the channel; and
   at least a first rod and a second rod having different diameters and configured to be interchangeably received in the channel and to be clamped by the fixation element;
   wherein when any one of the rods is received in the channel, the contact surface of the fixation element and the contact surface of the base contact the rod to clamp the rod in the channel;
   wherein the first rod and the second rod each have diameters within a range that is smaller than the first distance and sufficiently sized so as to be spaced apart from a bottom of the contact surface of the base when clamped in the channel; and
   wherein for all rods having a diameter within the range, the rod contacts the contact surface of the base only along two contact lines.

2. The anchoring assembly of claim 1, wherein said contact surfaces are shaped such that when the first rod or the second rod is clamped, the clamped rod contacts the contact surface of the fixation element along a third contact line.

3. The anchoring assembly of claim 1, wherein the fixation element has a projection on its side facing the rod, the projection being configured so as to be able to contact rods of different diameters.

4. The anchoring assembly of claim 1, wherein the cross section of the base is substantially V-shaped.

5. The anchoring assembly of claim 4, wherein side walls of the base which form the V-shape are curved.

6. The anchoring assembly of claim 1, wherein the contact surfaces are configured to clamp a plurality of rods with different diameters in a stepless manner.

7. The anchoring assembly of claim 1, wherein the head and the shaft are connected monoaxially.

8. The anchoring assembly of claim 1, wherein the shaft is pivotably connected to the head and wherein a pressure element is provided to lock the angular position of the shaft relative to the head and wherein the pressure element comprises the base for the rod.

9. The anchoring assembly of claim 1, wherein the rod has a substantially circular cross section.

10. The anchoring assembly of claim 1, wherein the shaft, the head and the fixation element are made of a biocompatible material.

11. The anchoring assembly of claim 1, wherein the base comprises an internal hole for providing a contact surface in two areas located on both sides of the legs, respectively.

12. The anchoring assembly of claim 1, wherein the diameter of the first rod is larger than the diameter of the second rod by about 14%.

13. The anchoring assembly of claim 1, further comprising a third rod having a diameter different than the diameters of the first rod and the second rod.

14. An anchoring assembly for anchoring a rod to a bone or a vertebra, the anchoring assembly comprising:
   a bone anchoring device comprising a shaft and a head pivotably connected to said shaft and having two substantially vertically extending legs spaced apart by a first distance and defining a channel;
   a pressure element having a recess including a base with a contact surface, the pressure element configured to lock the angular position of the shaft relative to the head;
   a fixation element having a contact surface facing the contact surface of the base of the pressure element, the fixation element secured to the legs and configured to move sufficiently into and out of the channel; and
   at least a first rod and a second rod having different diameters and configured to be interchangeably received in the channel when the head of the bone anchoring device and the pressure element are assembled, and to be clamped by the fixation element;

wherein when any one of the rods is received in the channel, the contact surface of the fixation element and the contact surface of the base of the pressure element contact the rod to clamp the rod in the channel;

wherein the first rod and the second rod each have diameters within a range that is smaller than the first distance and sufficiently sized so as to be spaced apart from a bottom of the contact surface of the base of the pressure element when claimed in the channel; and wherein for all rods having a diameter within the range and that are configured to be received in the channel when the head of the bone anchoring device and the pressure element are assembled, the rod contacts the contact surface of the base of the pressure element only along two contact lines.

15. The anchoring assembly of claim 14, wherein the contact surface of the fixation element is defined by a projection facing the contact surface of the base of the pressure element.

16. The anchoring assembly of claim 14, wherein the fixation element comprises an outer fixation member configured to lock the angular position of the shaft relative to the head, and an inner fixation member comprising the contact surface facing the contact surface of the base of the pressure element and configured to move sufficiently into and out of the outer fixation member to clamp the first rod or the second rod in the channel.

17. The anchoring assembly of claim 16, wherein the contact surface of the inner fixation member is defined by a projection facing the contact surface of the base of the pressure element.

18. The anchoring assembly of claim 14, wherein the diameter of the first rod is larger than the diameter of the second rod by about 14%.

19. A method of attaching a bone anchoring assembly to a bone or a vertebra, the anchoring assembly comprising a bone anchoring device comprising a shaft and a head connected to said shaft and having a recess with a base having a contact surface, the head further comprising two substantially vertically extending legs spaced apart by a first distance and defining a channel, a fixation element having a contact surface facing the contact surface of the base of the head, the fixation element secured to the legs and configured to move sufficiently into and out of the channel, and at least a first rod and a second rod having different diameters and configured to be interchangeably received in the channel and to be clamped by the fixation element, wherein when any one of the rods is received in the channel, the contact surface of the fixation element and the contact surface of the base contact the rod to clamp the rod in the channel, wherein the first rod and the second rod each have diameters within a range that is smaller than the first distance and sufficiently sized so as to be spaced apart from a bottom of the contact surface of the base when clamped in the channel, and wherein for all rods having a diameter within the range the rod contacts the contact surface of the base only along two contact lines, the method comprising:

attaching the bone anchoring device to a bone or vertebra;
inserting the first rod or the second rod in the channel; and
clamping the inserted rod in the channel with the fixation element.

20. The method of claim 19, wherein the diameter of the first rod is larger than the diameter of the second rod by about 14%.

21. An anchoring assembly for anchoring a rod to a bone or a vertebra, the anchoring assembly comprising:

at least a first rod and a second rod having different diameters;
a bone anchoring device comprising:
a shaft; and
a head connected to the shaft and having a recess with a base having a contact surface, the head further comprising two substantially vertically extending legs defining a channel for interchangeably receiving each one of the rods in the channel; and
a fixation element having a contact surface facing the contact surface of the base of the head, the fixation element secured to the legs and configured to move sufficiently into and out of the channel to interchangeably clamp each of the rods in the channel;
wherein the contact surface of the base has a substantially V-shaped cross-section and comprises a first side wall comprising a flat surface lying along a first plane extending from one of the legs towards a bottom of the base and a second side wall comprising a flat surface lying along a second plane extending from the other one of the legs towards the bottom of the base, wherein the second plane intersects the first plane; and
wherein when one of the rods is received in the channel, the contact surface of the fixation element and the contact surface of the base contact the rod to clamp the rod in the channel.

* * * * *